United States Patent [19]

Prince et al.

[11] Patent Number: 4,639,371

[45] Date of Patent: Jan. 27, 1987

[54] HEPATITIS B ANTIGENIC COMPOSITIONS AND VACCINES AGAINST HEPATITIS B DERIVED THEREFROM

[75] Inventors: Alfred M. Prince, Pound Ridge; John Vnek, Bronx, both of N.Y.

[73] Assignee: New York Blood Center, Inc., New York, N.Y.

[21] Appl. No.: 656,833

[22] Filed: Oct. 2, 1984

[51] Int. Cl.$^4$ .................. A61K 39/12; A61K 39/42; C07K 15/04

[52] U.S. Cl. .................. 424/86; 424/85; 424/89; 424/101; 530/387; 530/806; 530/403; 530/415; 530/417; 530/421; 530/380

[58] Field of Search .................. 260/112 R, 112 B; 424/85, 101, 86, 89, 88; 530/387, 806

[56] References Cited

U.S. PATENT DOCUMENTS

| | | | |
|---|---|---|---|
| 3,636,191 | 1/1972 | Blumberg et al. | 424/89 |
| 3,951,937 | 4/1976 | Vnek et al. | 260/112 B |
| 4,017,360 | 4/1977 | Bertland et al. | 435/212 X |
| 4,113,712 | 9/1978 | Funakoshi | 260/112 R |
| 4,118,477 | 10/1978 | McAleer et al. | 424/89 |
| 4,164,565 | 8/1979 | Prince et al. | 424/89 |
| 4,181,713 | 1/1980 | McAleer et al. | 260/112 B X |
| 4,442,205 | 4/1984 | Hamer et al. | 424/89 X |
| 4,490,361 | 12/1984 | Heldebrant | 424/101 |

OTHER PUBLICATIONS

Brummelhuis et al, Preparation of Hepatitis B Vaccine By Heat-Inactivation, pp. 51–57.

*Primary Examiner*—Howard E. Schain
*Attorney, Agent, or Firm*—Sprung Horn Kramer & Woods

[57] ABSTRACT

There are disclosed a process for enhancing the immunogenicity of a lipid membrane based immunogen comprising flash heating it at a membrane concentrations sufficient under the conditions of flash heating to result in melting of membranes and fusing the melted membranes into novel morphologic forms and a proteinaceous mass comprising particles of HBsAg, said particles including particles of HBsAg in morphologic form not found in nature, said HBsAg contains particles being filaments, branched filaments, closed circular or closed circular branched filaments.

44 Claims, 8 Drawing Figures

100 nm 100 nm 100 nm 100 nm

HEPATITIS B ANTIGENIC COMPOSITIONS AND VACCINES AGAINST HEPATITIS B DERIVED THEREFROM

BACKGROUND OF THE INVENTION

1. Field of the Invention

This invention relates to a solution or suspension of particles useful as a vaccine or vaccine intermediate. More especially, this invention relates to hepatitis B surface antigen (HBsAg) carrying particles in novel forms which are highly immunogenic. This invention relates to a process for the production of such particles, and to their use in a process for immunizing animals, e.g., humans and chimpanzees against hepatitis B virus (HBV).

2. Discussion of the Prior Art

The relationship between what is now referred to as the hepatitis B surface antigen (HBsAg) and hepatitis B virus was definitively identified many years ago by Alfred M. Prince (Pro. Nat. Acad. Sci (U.S.) 60:814–821, 1968). This antigen is primarily located on proteins embedded in the membrane of lipoprotein particles having a particle size of approximately 18 to 24 nm and filaments of a similar diameter. These are now known to represent fragments of membrane similar to that which surrounds the virion of HBV, also known as the "Dane" particle.

Thereafter, a vaccine containing such particles was disclosed in U.S. Pat. No. 3,636,191 by Blumberg et al. Prince and others thereafter disclosed other hepatitis B viral vaccines containing membrane proteins derived from Dane particles and filaments. These Dane particles and filaments contained or were associated with the hepatitis B e antigen found in many chronic carriers of the hepatitis B virus.

Since the work described above was conducted, a vaccine against the hepatitis B virus was introduced in the U.S. containing HBsAg particles. This vaccine is produced by enyzme digestion of HBsAg containing particles derived from the plasma of chronically infected HBV carriers, more or less as described in U.S. Pat. No. 3,636,191, supra. This vaccine is prepared by a costly purification process which results in substantial losses of its immunogenicity. As a result, a relatively large dose of the resulting antigen (HBsAg) must be administered to assure an adequate immune response. Because of these factors, the vaccine has been available only at a relatively high cost, about $30.00 per dose or higher. Since an original injection and two boosters are required, it presently costs approximately $100.00 to become immunized against the hepatitis B virus in the United States, a cost that is not affordable in those parts of the world where the need for this vaccine is greatest.

It has become desirable, therefore, to provide a hepatitis B vaccine containing hepatitis B surface antigen in a substantially pure form having greatly increased immunogenicity so that much smaller, less costly, doses can be used. It is, of course, also essential that the infective virus present in the starting plasma has been completely inactivated so as to present no risk of infection.

Hepatitis B infection affects, for the most part, individuals residing in developing countries in Asia and Africa where limited funds are available for public health measures. It is mandatory in this twentieth century to provide such a vaccine for the protection of the hundreds of millions of people who are at risk of infection by hepatitis B virus, and as a consequence suffer the risk of subsequent development of cirrhosis and liver cancer, and to provide this at a cost that is affordable. In many parts of the developing world this necessitates that immunization must cost less than $1.00 per person, if the vaccine is to be used.

SUMMARY OF THE INVENTION

In accordance with the foregoing, a vaccine or vaccine intermediate is provided by the invention which comprises particles containing HBs antigens, which have been to a large extent transformed into forms having a novel morphology, never found in nature, which has a surprisingly enhanced immunogenicity. The vaccine of the instant invention is characterized by the presence of less than 5% by weight of blood serum proteins, other than sodium caprylate stabilized human serum albumin and is preferably substantially free of blood serum proteins.

It has been discovered that by the particular mode of flash heating used for inactivating any live virus which might remain after purification that not only is the virus inactivated as determined by chimpanzee tests, but that a substantial percentage of the particles are converted into new morphological forms. These comprise 15–30 nm diameter filamentous forms which were not present prior to the heating step. These filamentous forms include the novel forms diagramatically illustrated in FIG. 1 and in the electron micrographs. These forms include straight filaments, closed circular or ring shaped filaments and branched filaments of many varieties.

Generally speaking, the percentage of HBsAg containing particles which are in the form of such bizarre filamentous structures is between 15 and 75% as determined by electron microscopy. Preferably, HBsAg containing particles which have been converted into these novel filamentous structures account for more than 50% of the total HBsAg containing particles.

The vaccine of the present invention can be characterized, additionally, in terms of the manner by which it is made. Generally speaking, the vaccine is produced by the steps of:

A. Precipitating HBsAg from blood plasma, e.g., human blood plasma containing the same by contacting the same with polyethylene glycol to separate HBsAg from other blood serum proteins contained therein;

B. Affecting negative adsorption of such separated HBsAg on hydroxylapatite to further remove the bulk of serum proteins;

C. Subjecting the so adsorbed HBsAg to isopynic centrifugation to separate remaining intact Dane particles, and to further remove the remaining traces of contaminating serum proteins;

D. Subjecting the particles so separated by centrifugation to heat inactivation by heating them while a concentration of 0.5–10 mg/ml at a temperature of 101° to 104° C. for 2 to 5 minutes and thereafter cooling the heated particles, e.g., by introducing them into an ice water bath.

Steps A through C supra are important because it is through these that the HBsAg is purified so that the mass undergoing heat treatment contains less than 5% by weight of other serum proteins. Stated differently, the mass being heat treated contains at least 95%, preferably more than 99% of HBsAg particles, based on the total weight of protein. Preferably, the HBsAg is undiluted with other proteins, however, one may add sodium caprylate treated albumin as an additional stabilizer. Ideally, the composition which is treated in the heat inactivation step (step D) can be characterized by its purity, especially the absence of other blood plasma proteins.

The heat inactivation step of the product of steps A-C, however, not only contributes to the safety of the vaccine, but most importantly enhances the immunogenicity of the vaccine. This inactivation step is preferably carried out at 101° to 104° C. by passing the purified particle solution resulting from step C through a 2 mm diameter tube, (e.g., brass or stainless steel etc.) immersed in a 101° to 104° C. heated medium, (e.g., oil bath) for a total dwell time of 2.5 to 6.0 minutes. It is of importance to the invention that the HBsAg protein concentration of the solution heated must be between 0.1 and 10 milligrams per ml, preferably about 0.5 to 6.0 mg/ml. It should be recognized that in employing a procedure as described, some time is required to heat the solution inside the tubing up to 101° to 104° C. and hence, the "total dwell time" will be longer than the time at which the solution is actually heated at 101° to 104° C. The difference will, of course, depend on flow rate.

It should be recognized that continuous flow flash heating must be carried out at elevated pressure to prevent vaporization of the solution when it is brought to temperatures above 100° C. This is easily accomplished by the use of a high pressure liquid chromatography pump and a hydrostatic pressure head emanating from the receiving vessel.

Optionally, an additional inactivation can be carried out by treating the purified antigen from step C with a detergent such as Tween 80, e.g., adding an equal volume of a solution of 2% Tween 80 in water. This treatment further enhances the safety of the vaccine. It is preferred, however, to eliminate the detergent treatment as the resultant product is more immunogenic if the inactivation procedure is carried out without detergent treatment.

Following the flash heat inactivation step, the recovered purified and virus inactivated particle solution can be adjuvanted by adsorptioon to aluminum phosphate or aluminum hydroxide gels, if desired. For use in tropical countries, it may be desirable to lyophilize the vaccine prior to addition of alum gels, and to add the latter after rehydration, if desired.

Thereafter, it is worked up as a final vaccine by dilution with a physiologically acceptable medium, such as, 0.15 Molar NaCl.

As a final guarantee of safety, it is desirable to subject the alum adsorbed vaccine, in final bulk, or in final containers, to an additional heat inactivation step, i.e., exposure to 65° C. for 10-18 hours. The final "pasteurization" step is known from chimpanzee studies to be capable of inactivating about 10,000 infective doses of HBV, and has little or no effect on the immunogenicity of the vaccine.

In the final vaccine the HBsAg containing protein concentration is 0.1 to 10 micrograms per ml. A suitable dose for injection depends upon the age of the recipient. For an adult male, a typical dose has between 1 and 10 micrograms of HBsAg, and can be introduced intramuscularly, subcutaneously or intradermally.

BRIEF DESCRIPTION OF DRAWINGS

Referring to the drawings appended hereto.

DESCRIPTION OF SPECIFIC EMBODIMENTS

Figure 2:
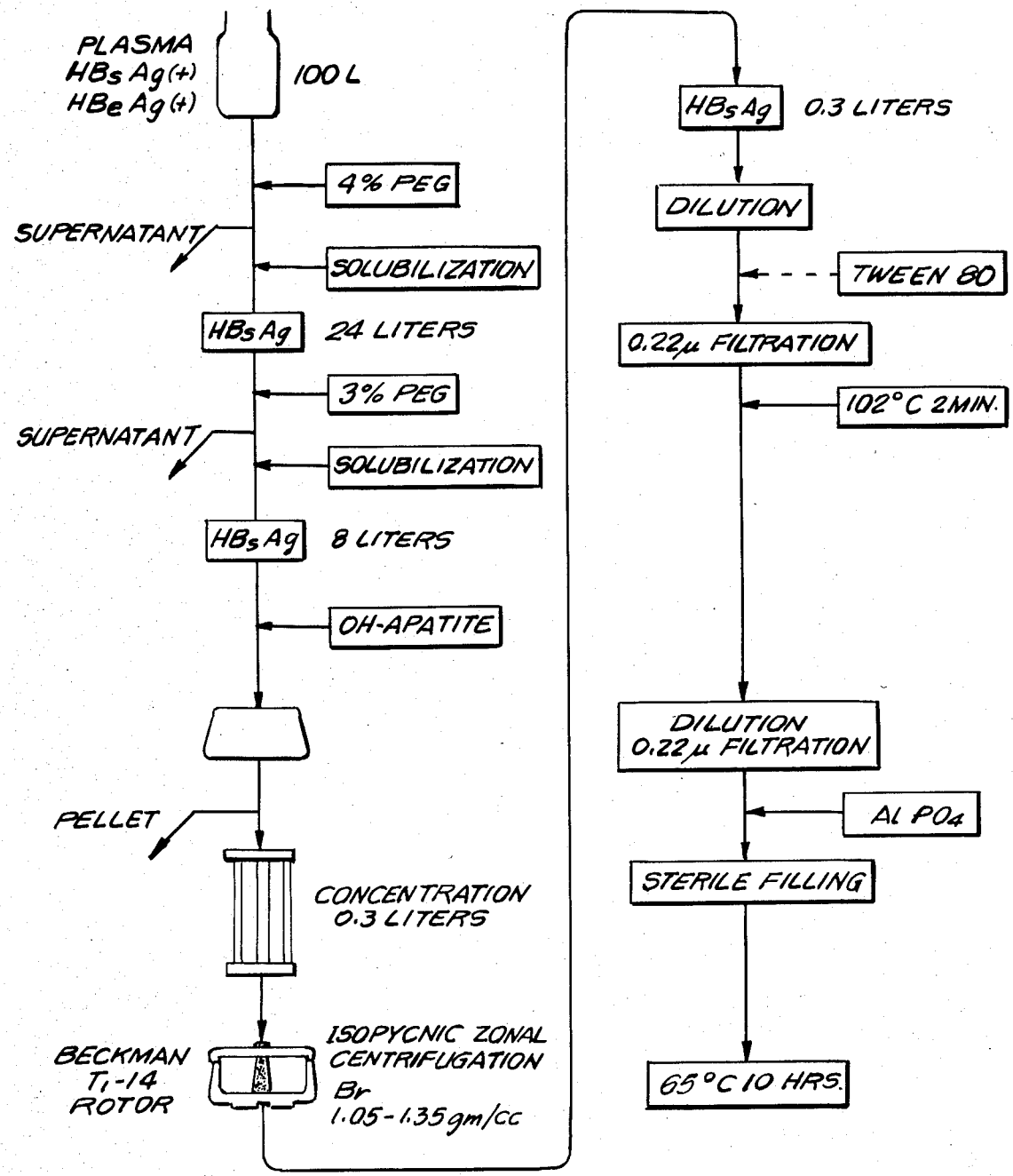
FIG. 2 is a flow diagram showing a method for the preparation of the vaccine according to the invention.

The invention will now be described with reference to FIG. 2. Typically, 100 liters of plasma containing HBsAg, preferably also containing hepatitis B e antigen (HBeAg), are treated, after adjustment to pH 4.6, and clarification in a continuous flow centrifuges, with polyethylene glycol (molecular weight 2000 to 8000) at a concentration of 3 to 8%, to yield a precipitate. The precipitate contains the HBsAg containing particles. The supernatant liquid containing other blood serum proteins is removed and the precipitate is re-solubilized by adding distilled $H_2O$ to bring the volume to 24 liters and adjusting the pH to 7.5-8.0. The solution is then adjusted to pH 5.0 and the resulting precipitate is removed.

Thereafter, the composition is treated with polyethylene glycol (molecular weight 2000 to 8000) to adjust the polyethylene glycol content to 2.5 to 6 weight percent after adjustment of pH to 3.5-5.0, optimally 4.6 to form a second precipitate containing HBsAg. From this, a supernatant liquid containing residual blood serum proteins is removed. The second precipitate is solubilized after a pH 5.0 precipitation step as above by adding distilled water, adjusting to pH 6.0 to 8.0, ideally pH 6.8, to a total volume of 8 liters.

The HBsAg containing solution in 0.005 M phosphate buffer pH 6.8 is then brought in contact with packed hydroxylapatite. The supernatant, together with 0.02 and 0.05 M phosphate buffer wash solutions are then concentrated by diafiltration to 0.3 liters and subjected to flotation isopynic zonal centrifugation.

In this step concentrated HBsAg is adjusted to a density of 1.23 to 1.30 g/ml with solid KBr and dynamically loaded under a linear 1.05 to 1.2 g/ml KBr gradient over a 1.3–2 g/ml cushion in a rotor. The gradient is centrifuged for 16 to 24 hours, at 25,000 to 35,000 RPM and fractionated by pumping water into the center of the rotor. Fractions corresponding to densities between 1.17 and 1.22 g/ml are pooled.

The resultant fractions are adjusted to a volume of 1 to 10 liters in normal saline in order to dilute the HBsAg to a concentration of 0.5 to 10 mg/ml. Thereafter, optionally the solution may be treated with an equal volume of Tween 80 detergent or other zwitterionic detergent, employing an aqueous solution thereof at a concentration of 1 to 3 weight percent. The HBsAg containing mass is permitted to be in contact with the detergent for between 0.5 and 24 hours at 4° to 25° C.

Thereafter, the composition is subjected to filtration through a 0.22 micron filter and subjected to heat inactivation by heating the same at 101° to 104° C. for 1 to 15 minutes, optionally for 2 to 5 minutes, while the composition is passed through a 0.1 to 10 mm, optionally 1 to 3 mm diameter stainless steel tubing resting in an oil bath maintained at 102° to 105° C., under pressure, as described above. The pressure must be sufficient to prevent boiling, i.e., 800 to 1000 mm Hg, especially 900 to 1000 mm Hg.

The so heated mass is then cooled, such as by collection of the heated solution into a vessel resting in an ice water bath. Generally, cooling to 2°–4° C. is affected within 5 minutes following cessation of the heat treatment. However, it may be derived to pass the solution through a second coil in a bath set at any derived temperature between 20° and 100° C., especially 75°–90° C. to achieve optimal results.

The purified and flash heat inactivated HBsAg containing material is then adjuvanted suitably by the use of an aluminum phosphate adjuvant. Generally, a presterilized aluminum phosphate is added to the inactivated diluted antigen under sterile conditions to provide 0.3 to 0.6 mg aluminum phosphate per ml of diluted antigen. Thereafter, the adjuvanted composition is sterile filled into suitable containers. The final containers are further held for 10 hours at 65° C. ("pasteurization") as an additional sterilization step to further assure safety of the final product. The vaccine is maintained at a temperature of 2° to 6° C. for up to 3 years prior to use in immunization.

As a result of purifying the HBsAg in the manner described above and subjecting relatively pure HBsAg containing particles at a concentration of 0.1 to 10 mg/ml to the described heat treatment, unusually shaped HBsAg particles result as shown in FIGS. 4 through 7. Whereas the initial HBsAg containing particles are generally spherical and largely of a size of 18 to 24 nm (FIG. 3), particles derived by the process of the invention are predominantly transformed into polymorphous filaments, as seen especially in FIGS. 1, 4 and 6. Especially remarkable are the heretofore unseen filaments, as seen in FIGS. 4 through 7, especially FIG. 5. Such filaments which contain HBsAg antigenicity are characterized by being branched, or ring shaped. They can be curvilinear or rectilinear in configuration. Generally speaking, the filaments have a length of at least 50 nm and are generally between 100 and 1000 nm.

When the filamentous structures are branched, they are branched with a structure having a length of at least 50 nm and frequently 100 to 300 nm. Some of the filaments obtained by the process of this invention have at least three branches per filament structure and have an irregular configuration, the minimum length of which is at least 100 nm and is preferably 200 to 1000 nm.

It should be emphasized that such branched or circular (ring shaped) filaments have never been seen in serum derived HBsAg associated particles without this form of flash heat treatment.

Referring to the electron micrographs of FIGS. 4 through 7, it will be observed that the HBsAg containing particles of the invention include ring shaped particles, branched filaments and linear filamentous particles, as well as spherical 16–25 nm HBsAg particles.

The novel morphological forms include ring shaped particles which have filamentous portions protruding therefrom. These filamentous particles usually have a length of at least 50 nm and generally are 100 to 300 nm in length.

When detergent treatment is used the non-branched filamentous can be further characterized by a density at 20° C. of between 1.210 and 1.230 Gm/cc (mean 1.224 Gm/cc) and thus, are distinguished from non-branched filaments seen in plasma of some chronic HBsAg carrier who have so called Dane particles and/or associated filaments. The latter have a mean density of 1.200.

The "ring shaped" particles include those which form a substantially perfect circle or ring as well as others which substantially enclose a region. The area defined by the surrounding HBsAg containing mass can be any shape including elliptical and donut-shaped, i.e., it can have a regular or irregular configuration.

The novel morphological forms observed differ dramatically from previously described micellar particles. The latter are characterized by a central hub composed of hydrophobic ends of polypeptide chains, the hydrophilic portions of which extend towards the surface of roughly spherical particles whereas the filaments prepared according to the invention are not connected to a central hub. Some filaments are in the form of irregular, rings which themselves can have protruding filaments. However, normally there are no more than three, usually two or only one such protruding filaments. Of course, the particles of the invention do not have a dense compacted core with outwardly projecting filaments.

In order to more fully illustrate the invention and the manner of practicing the same, the following examples are presented:

EXAMPLE 1

Pooled plasma containing both HBeAg and HBsAg obtained from chronic HBsAg carriers is adjusted to pH 4.6 and clarified at 10,000 RPM in a Westphalia continuous flow centrifuge. The clarified supernatant is adjusted to final concentration 4% PEG 6000 at 4° C. and stirred for 20 minutes. The precipitate is recovered by sedimentation for two hours without centrifugation and is solubilized in 1/5th of the original volume with distilled water by adjusting the pH to 7.5–8.0. The pH is then lowered to 5.0 and the resulting precipitate is recovered by centrifugation. The pH of the supernate is then adjusted to 4.6 and PEG is added to a final concentration of 3%.

After sedimentation overnight at 4° C., the precipitate is redissolved by neutralization and the suspension clarified after lowering the pH to 5.0 as before. The material is adjusted to pH 6.8 and after addition of 0.005 M phosphate buffer further purified by 2–3 consecutive adsorptions with equal volumes of packed hydroxylapatite. Subsequently, the hydroxylapatite sediments are washed with 0.02 and 0.05 M phosphate buffer. Finally, the original supernatants and the washes of the hydroxylapatite sediments are pooled, clarified by centrifugation and concentrated to about 0.3% of starting plasma volume with an Amicon hollow fiber cartridge. The concentrated HBsAg is then adjusted to a density of 1.25 gm/ml with solid KBr and dynamically loaded under a linear 1.05 to 1.2 g/ml KBr gradient over a 1.3 g/ml cushion into a Beckman Ti-14 rotor. The gradient is centrifuged for 18 hours at 28,000 rpm and fractionated by pumping water into the center of the rotor. Fractions corresponding to densities between 1.17 and 1.22 g/ml are pooled.

The purified antigen is adjusted to a concentration of 1 mg/ml (based on $OD_{280}$, $E_{1\ cm}^{0.1\%} = 3.73$) and diluted with an equal volume of 2% Tween 80 detergent. This detergent treatment strips outer membranes from Dane particles, thus rendering them non-infectious. It also changes the aqueous density of the remaining particles from a mean of 1.200 g/ml to 1.224 g/ml as a result of the removal of some lipid. After 1 hour at room temperature, the solution is filtered through a 0.22 micron Millipore filter. Thereafter, the purified antigen is passed under 950 mm Hg pressure through a 2 mm diameter stainless steel coil suspended in an oil bath maintained at a temperature of 102° C. at a rate such that the material is held at 102° C. for 2 minutes. This requires a total dwell time of 2 minutes, 40 seconds. Following dilution, the resultant composition is adjuvanted with sterile aluminum phosphate. The final alum adsorbed vaccine is further treated for 10 hours at 65° C. as an additional virus inactivation step.

COMPARATIVE EXAMPLE 2

Figure 3:
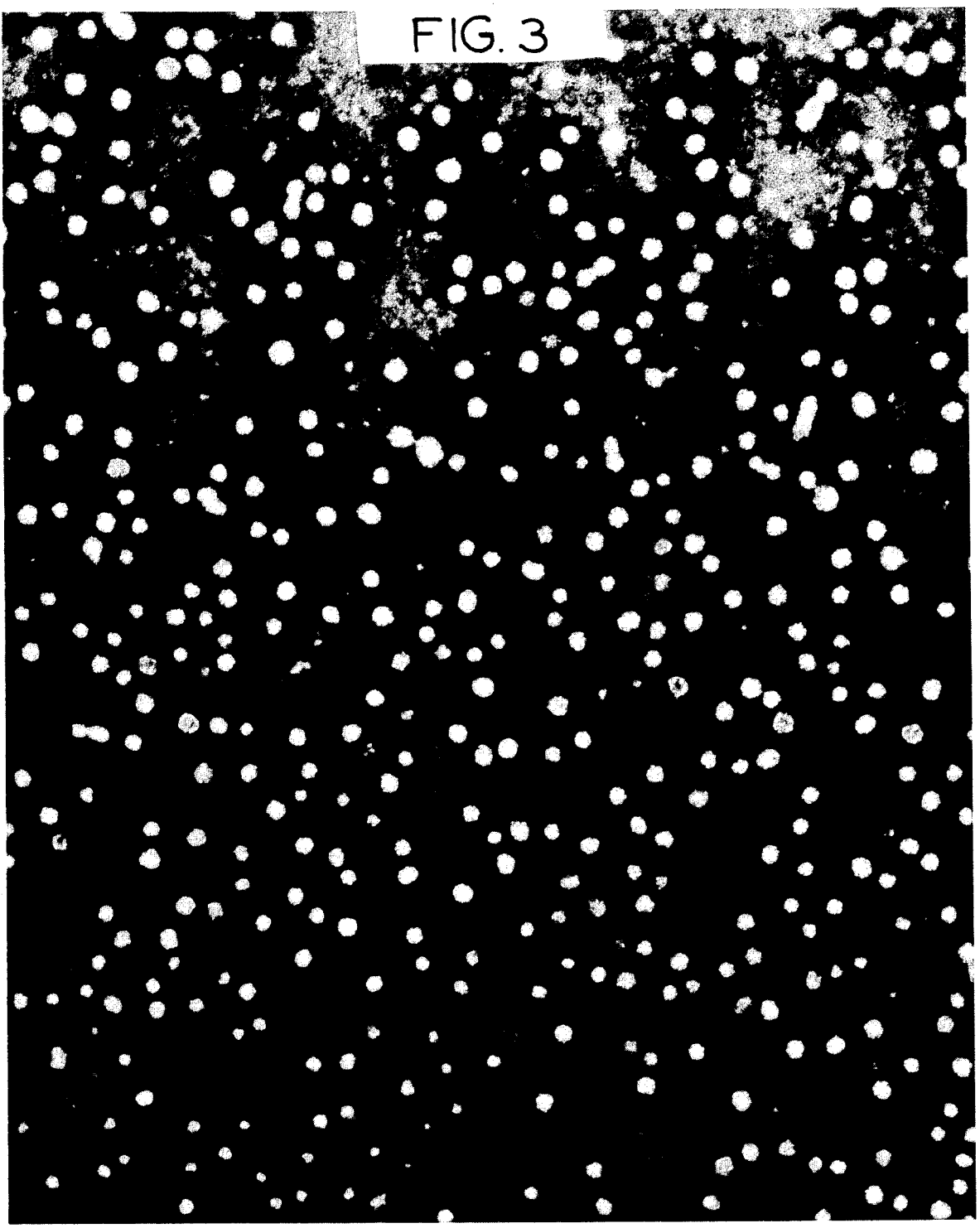
FIG. 3 is an electron micrograph of phosphotungstic acid negatively stained HBsAg containing particles obtained following steps A-C above, which were not subjected to the flash heat treatment of the invention and contain HBsAg particles in the form predominantly of 18 to 24 nm spherical particles.

The procedure of Example 1 is repeated substantially except for the heat inactivation step at 102° C. and the steps following. There is obtained a HBsAg containing mass having a protein concentration, as expressed in Example 1, of 1.18 mg/ml. The purity of the HBsAg is equal to or greater than 95%, based on gel diffusion study with polyvalent and monovalent anti-human serum protein anti-sera. The composition is, therefore, largely free of detectable amounts of human serum proteins. A portion of the sample is subjected to electron microscopy at 195,000× magnification after negative staining with 2% phosphotungstic acid. An electron micrograph of this sample is shown in FIG. 3.

EXAMPLE 3

Figure 4:
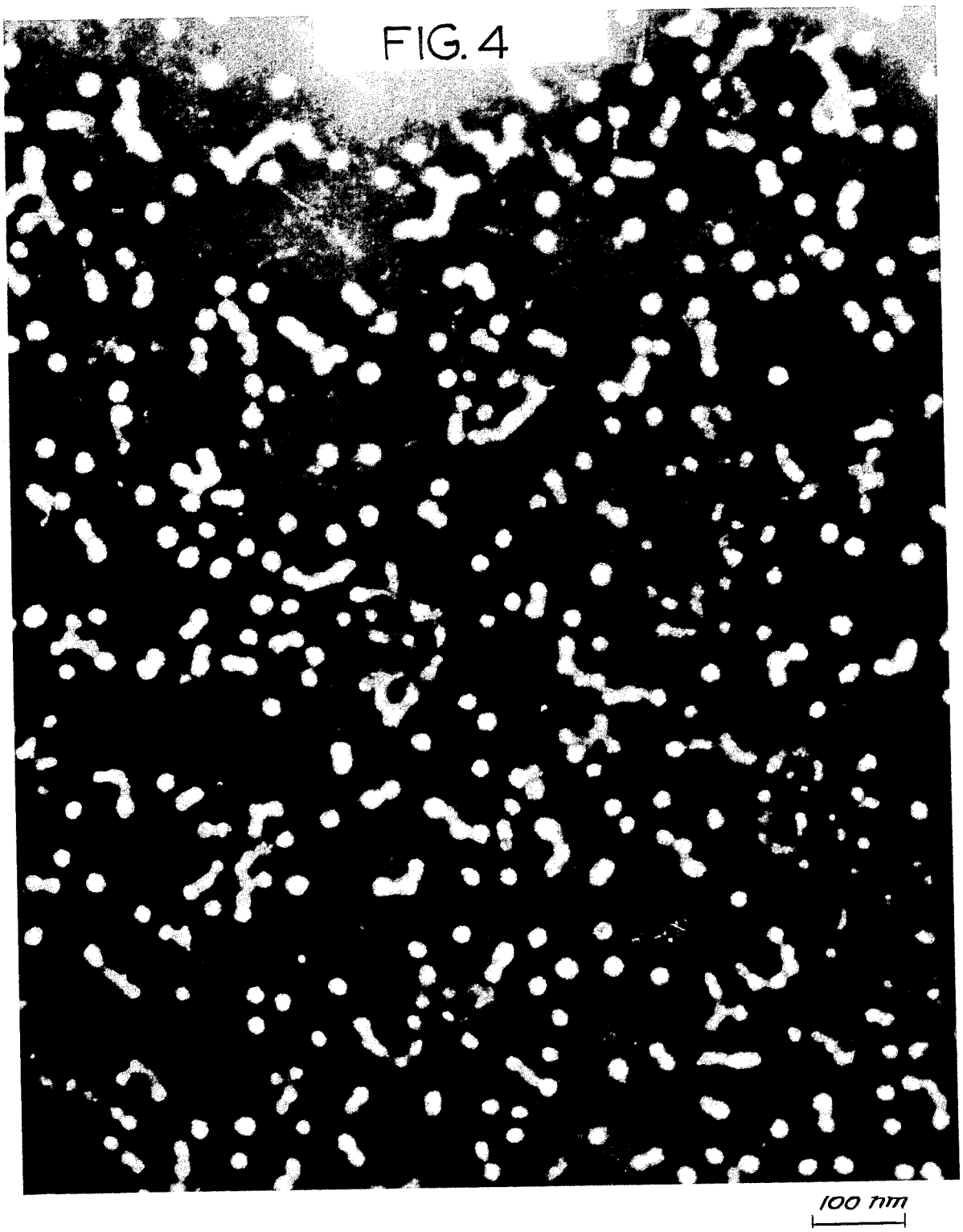
FIG. 4 is an electron micrograph, similar to FIG. 1, showing the form of the HBsAg containing particles when subjected to the heat treatment, showing the particles transformed into linear, branched and circular filamentous forms.

A portion of the sample described in Example 2 is thereafter subjected to a heat treatment by exposing it to 102° C. by passage through a 2 mm diameter stainless steel tubing immersed in an 102° C. oil bath for a total dwell time of two minutes forty seconds. Forty seconds is required to reach the 102° C. temperature. Hence, the protein composition is heated at 102° C. for about two minutes. The sample becomes slightly opalescent, indicative of some aggregation. A portion of the sample is negatively stained and electron microscopic photographs are taken thereof. As shown in FIG. 4, linear, branched generally circular filamentous forms of surface antigen particles appear after heating. These particles are not present in the original preparation. These particles result from actual membrane fusion rather than simple aggregation since even 30 minutes of exposure to ultrasonication does not affect their morphology.

To determine the relative immunogenicity of the filamentous and spherical particles, these are partially separated from each other by centrifugation.

EXAMPLE 4

The heated preparation of Example 3 is centrifuged at 8,000 g for 20 minutes and separated into a supernatant fraction which is furthered filtered through a 0.22 micron Millipore membrane after addition of 50 μl/ml of Tween 20 to reduce losses from filtration. A portion of this supernatant fraction is negatively stained and subjected to electron microscopy resulting in the electron micrograph of FIG. 5.

EXAMPLE 5

Figure 5:
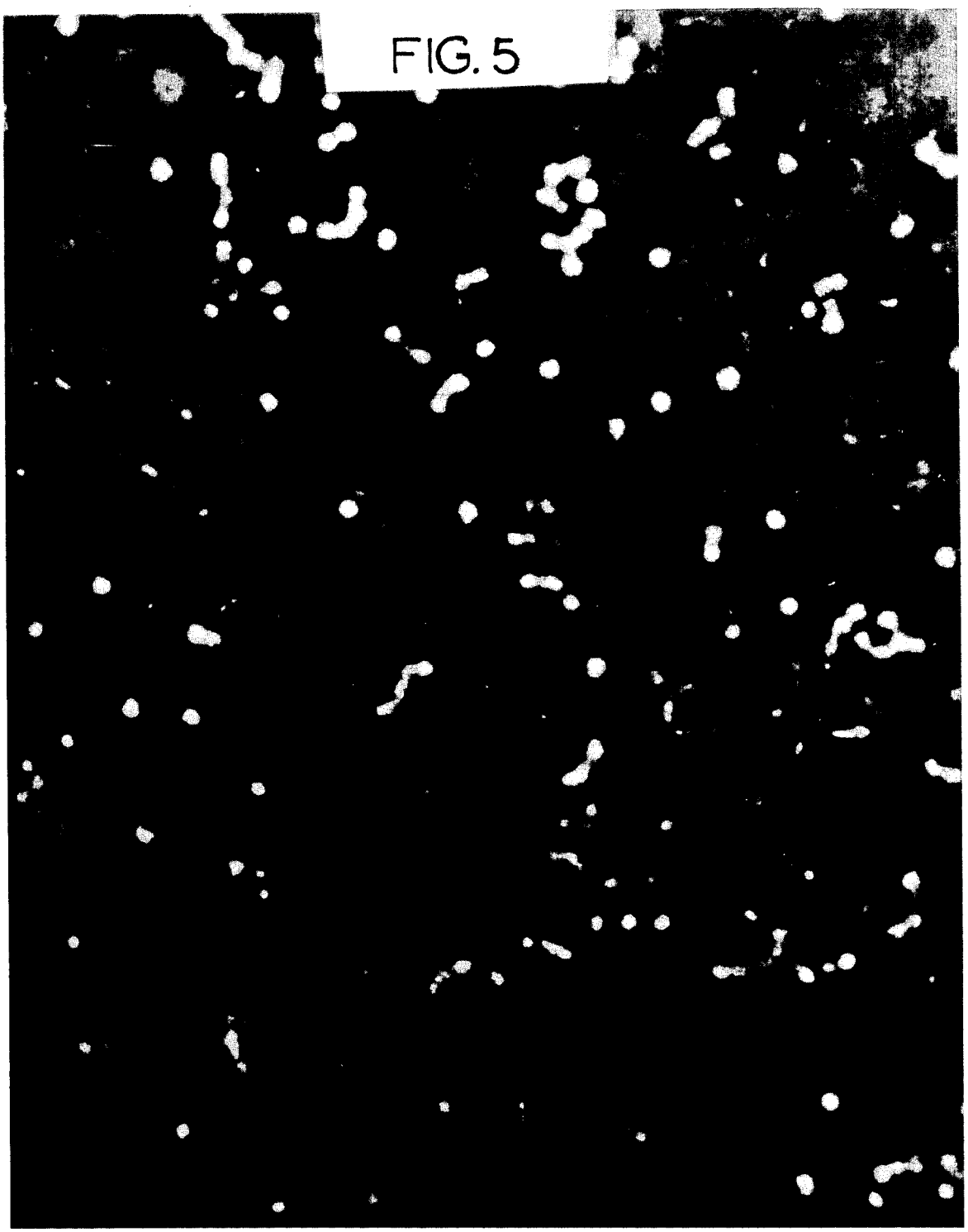
FIG. 5 is an electron micrograph, similar to FIGS. 3 and 4, of a supernatant fraction obtained after centrifuging the solution shown in FIG. 4 for 20 minutes at 8000 g and filtering the resultant supernatant.

The sediment from the filtration of Example 4 is resuspended in isotonic saline to original volume and, following negative staining, subjected to electron microscopy to produce the electron microscopic photograph of FIG. 5.

EXAMPLE 6

Flash Heat Inactivation in the Presence of Albumin

Figure 7:
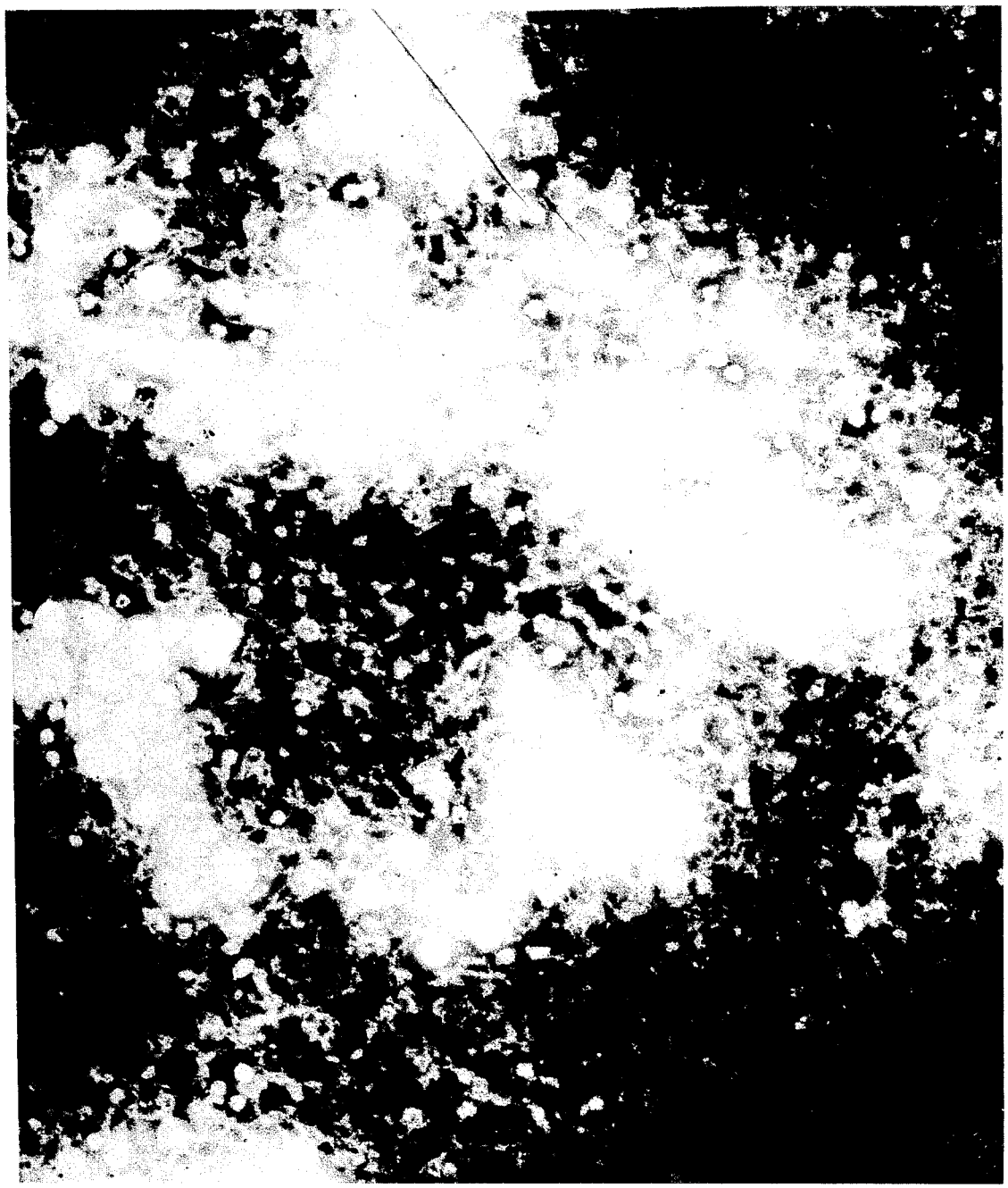
FIG. 7 is an electron micrograph similar to FIGS. 3 through 6, showing HBsAg containing particles prepared by this invention wherein the HBsAg particles were flash heat treated in the presence of 3 mg/ml of sodium caprylate treated serum albumin. The same morphological structures were obtained.

A preparation was flash heated as described in Example 3 in the presence of 3 mg/ml of human serum albumin, stabilized by sodium caprylate. Polymorphic filamentous forms were again produced (FIG. 7).

EXAMPLE 7

Preparation of Adjuvanted Proteinaceous Compositions 30 micro liters of the composition of Examples 2 and 3, 40 micro liters of the composition of Example 4 and 90 micro liters of the composition of Example 5 are added each to 10 ml of sterile normal saline to yield an estimated 4 micro grams per ml based on $OD_{280}$. This is recognized to be an approximate estimation of protein concentration due to the opalescence resulting from the heating process. More exact protein contents of these samples are obtained by the BIORAD protein assay. The solutions are adjusted with equal volumes of aluminum phosphate gel (1.2 mg/ml), prepared by the Rijks Inst. voor de Volksgesundheid of Bilthoven, Holland, to yield an estimated 1 micro gram / 0.5 ml dose adsorbed to 0.3 mg alum phosphate gel.

Dilutions in saline containing ¼ and 1/16 the amount of each antigen are similarly adsorbed to alum adjuvant as above to give estimated doses of 0.25 and 0.6 micro grams. A control is also prepared with saline instead of antigen solution.

INOCULATION OF MICE

Groups of 20 female ICR Swiss mice weighing 20–22 grams are inoculated intraperitoneally with 0.5 cc of the various preparations. Thus, each sample is inoculated into 60 mice, 20 receiving each of the three dilutions. Ten mice received the control adjuvant.

All mice are bleed by cardiac exsanguination. The blood is collected into individual tubes, allowed to clot at room temperature and held over night at 4° C. prior to recovery of serum from the centrifuged (3,000 rpm, 15 min) clots.

Each serum is tested by a quantitative parallel line radioimmunoassay using AUSAB ® test kits (Abbott Laboratories, Chicago, Ill.), in comparison to the WHO International HBIG standard containing 100 international units (IU) per ml. Samples giving radioactivity greater than that within the linear curve relating dilution and counts per minute (CPM) minus negative control mean CPM were retested at 1:10 and 1:100 dilutions. HBsAg antigenicity of samples was estimated by a parallel line radioimmunoassay using AUSRIA ® test kits (Abbott Laboratories, North Chicago, Ill.) in comparison to a provisional HBsAg/ad standard provided by the U.S.F.D.A. Results obtained with this standard are identical to those which have been independently obtained using the German National HBsAg/ad standard.

Figure 6:
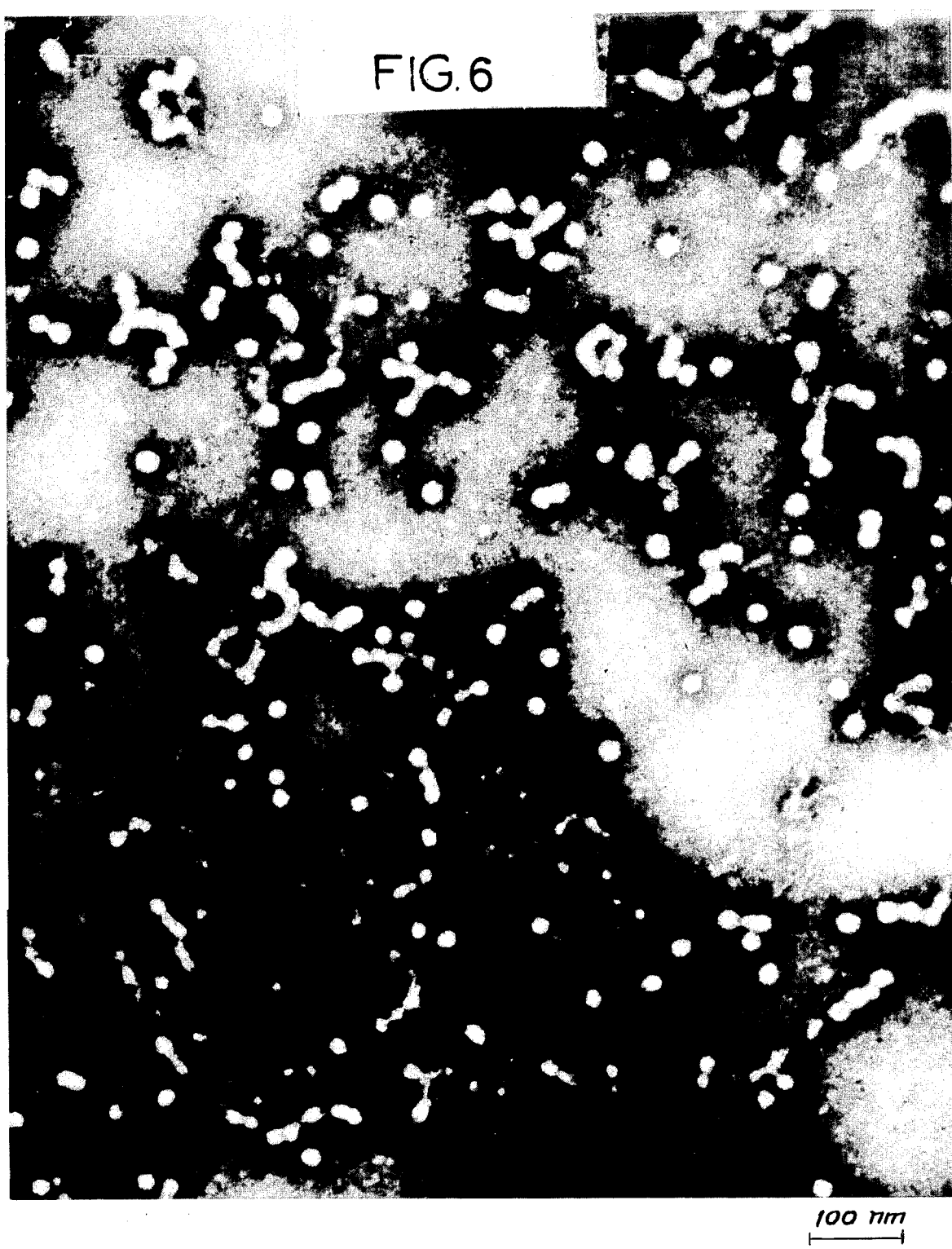
FIG. 6 is an electron micrograph similar to FIGS. 3 through 5, of the sediment obtained from centrifugation for 20 minutes at 8000 g resuspended in isotonic saline to original volume.

Table 1 below sets forth the protein content and the antigenicity of the different samples of Examples 2 through 5 and the ratio between these, i.e., "specific antigenicity". It may be seen that heating reduces the specific antigenicity by about 50%. This is particularly evident for Example 5 which has enriched filamentous forms, as seen by FIG. 6.

Figure 8:
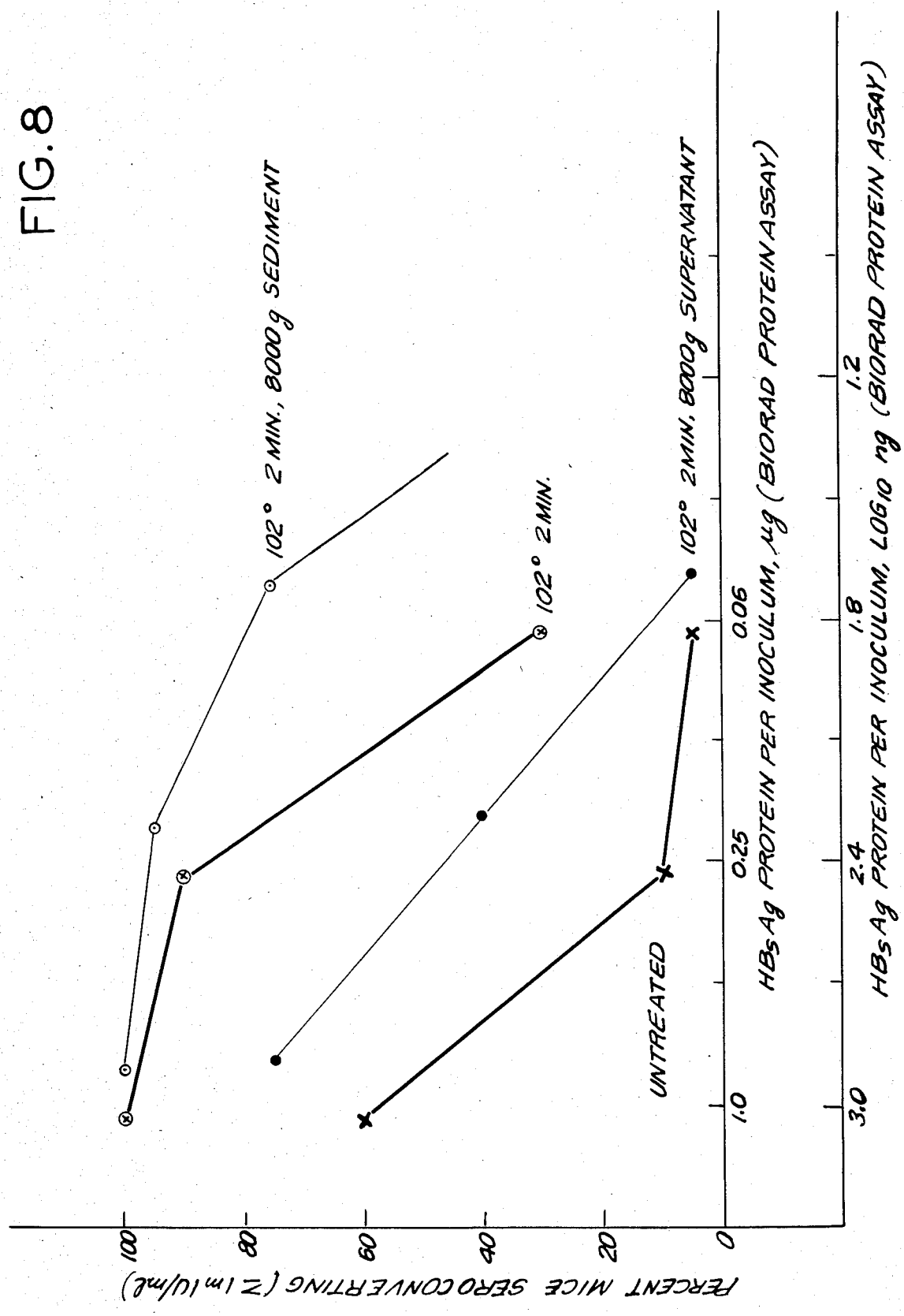
FIG. 8 shows the effect of heat inactivation on immunogenicity of purified HBsAg in mice of the preparations whose morphology was illustrated in FIGS. 3-6.

FIG. 8 shows the percent of mice developing at least 1 mIU/ml of anti-HBs 28–30 days after a single injection of dilutions of the four preparations. The heat treated preparation is seen to have a markedly enhanced immunogenicity by this criterion. Estimation of the dose required to seroconvert 50% of the mice reveals that heat treatment results in a 7.4 fold potentiation of immunogenicity, as revealed by the data of Table 2 below. The filamentous fraction (Example 5) was the most immunogenic, with a 29.5 fold potentiation.

4 to 10 fold, preferably 6 to 8 fold greater than the immunogenicity of a proteinaceous mass consisting essentially of spherical HBsAg particles of 18–24 nm in diameter. Of course, by separating the filamentous structures of the invention from the spherical 18–24 nm particles, the resultant composition can have an even greater enhanced immuonogenicity on the order of 20 to 30 fold, as evidence by the data supra in respect of the composition of Example 5.

Thus, it was surprisingly found that by inactivating HBsAg purified by the route of the invention at 102° C. for 2 minutes as described not only did the residual infectivity drop as was intended, but a dramatic increase in immunogenicity was unexpectedly obtained. This enhanced immunogenicity permits the formulation of vaccine of lower protein content and, thus, reduces the overall cost of the vaccine's production so that it is well below that of currently available vaccines.

EXAMPLE 8

Comparative Evaluation of Heat Inactivated Vaccine obtained by another Purification Technique and similar, but different Heat Inactivation Technique with Inactivation of Purified Antigen obtained by the Steps of this Invention HBsAg was purified by the procedure described supra by precipitation twice with polyethylene glycol followed by purification by negative adsorption to hy-

TABLE 1

| | | Effect of Heating on Specific Antigenicity | | | |
|---|---|---|---|---|---|
| | | HBsAg Protein[1] | HBsAg Antigenicity[2] | Specific Antigenicity[3] | |
| Example | Material | (mg/ml) | (mg/ml) | | % of original |
| 2 | Untreated HBsAg | 1.44 | 0.55 | 0.38 | 100 |
| 3 | 102° C. 2 min Rx HBsAg | 1.44 | 0.27 | 0.19 | 50 |
| 4 | 102° C. 2 min 8000 g supernatant | 0.74 | 0.23 | 0.31 | 81 |
| 5 | 102° C. 2 min 8000 g sediment | 0.35 | 0.02 | 0.06 | 16 |

[1]By BIORAD Protein Assay
[2]By parallel line radioimmunoassay (RIA) using AUSRIA Tests in comparison to FDA provisional HBsAg/ad standard.
[3]Specific Antigenicity: μg HBsAg by RIA vs. HBsAg/ad standard/μg HBsAg protein by BIORAD Protein Assay.

TABLE 2

| | EFFECT OF HEAT INACTIVATION OF PURIFIED HBsAg ON IMMUNOGENICITY IN MICE: SUMMARY | | | |
|---|---|---|---|---|
| EXAMPLE | MATERIAL | $\log_{10}$ ng/mouse | ng/mouse | POTENTIATION FACTOR |
| | (A) EFFECT ON DOSE REQUIRED FOR 50% SEROCONVERSION ($ED_{50}$) | | | |
| | | ESTIMATED $ED_{50}$ | | |
| 2 | Untreated HBsAg | 2.91 | 813 | 1.0 |
| 3 | 102° C. 2 min Rx HBsAg | 2.04 | 110 | 7.4 |
| 4 | 102° C. 2 min 8000 g supernatant | 2.46 | 288 | 2.8 |
| 5 | 102° C. 2 min 8000 g sediment | 1.44 | 27.6 | 29.5 |
| | (B) EFFECT ON MEAN ANTI-HBs LEVELS IN RESPONDERS | | | |
| | | ESTIMATED DOSE GIVING 1.5 $\log_1$ mIU/ml | | |
| 2 | Untreated HBsAg | 3.18 | 1500 | 1.0 |
| 3 | 102° C. 2 min Rx HBsAg | 2.40 | 250 | 6.0 |
| 4 | 102° C. 2 min 8000 g supernatant | 2.46 | 288 | 5.2 |
| 5 | 102° C. 2 min 8000 g sediment | 1.95 | 89 | 16.8 |

From the data above, it is concluded that heating of substantially pure HBsAg particles obtained by the separation procedure described above actually increases the immunogenicity of the HBsAg so that higher antibody levels are provided. A quantitative parameter is derived by estimating the dose required to produce a geometric mean anti-HBs level of 1.5 $\log_{10}$ mIU/ml (32 mIU). Using this parameter, heating at 102° C. for 2 minutes is estimated to increase immunogenicity 6-fold. Thus, the proteinaceous masses of the invention can be characterized as having an immunogenicity droxylapatite and submitted to purification by isopynic centrifugation. This partially purified material is identified herein as Sample A.

Another partially purified HBsAg composition, identified herein as Sample B, was made by the method described by Brummelhuis et al. (Preparation of Hepatitis B Vaccine by Heat Inactivation in *Hepatitis B Vaccine*, in Serum Symposium No. 18., Eds. P. Maupas and P. Guesry, Elsevier/North-Holland Biomedical Press, 1981).

Sample A was diluted with phosphate buffered saline to 1 mg/ml, 2 mg/ml, 4 mg/ml and 6 mg/ml and subjected to heat treatment as described below. Sample B was subjected to the heat treatment using the resuspended final pellet of HBsAg adjusted to a concentration of 20 µg HBsAg/ml as specified by the Brummelhuis procedure.

Samples A and B were placed into metal tubing with an internal diameter of 2 mm, extended with a short length of silicon rubber tubing, sealed with metal screw clamps. Heat inactivation was accomplished by immersing the tubes into a thermo stabilized oil bath heated to 102° C. The residence time of Samples A and B while at a temperature of 102° C. was two minutes. Thereafter, they were transferred to an ice water bath for cooling.

Samples of the resultant products were subjected to electron microscopy after negative staining in the same manner as FIGS. 3 through 6, i.e., with phosphotungstic acid negative stain. The electron micrograph of Samples A (1-6 mg/ml) revealed the same polymorphic filaments shown in FIGS. 4 through 6. The inactivated sample prepared according to the procedure of the Netherlands Red Cross, Sample B, contained in addition to HBsAg at least about 3 mg/ml of other serum proteins. The electron microscopy photograph thereof revealed substantially no filamentous particles of HBsAg. It has been found that addition of sodium caprylate stabilized albumin to 1-3 mg/ml, as in Example 6, does not alter the transformation to the polymorphous forms (FIG. 7), or the enhancement of immungenicity. It was concluded that the manner by which the HBsAg is purified as well as the concentration at which it is heated, determines of whether upon subsequent flash heat treatment, the HBsAg particles are converted into the novel and unusual morphological forms shown in FIGS. 4 through 6. Thus, heat inactivation is not per se determinative of the morphological effect, but rather the novel morphological forms which account for the improved immunogenicity result from a combination of the purification technique and actual heat inactivation procedure used.

The foregoing describes the best mode presently contemplated for carrying out the invention. In initial studies which gave rise to the unusual morphological forms of HBsAg, the purified HBsAg was diluted with a compatible protein, e.g., serum albumin to guard against any deleterious effects that the heat inactivation might have on the HBsAg, i.e., to protect the same against denaturation. Subsequently, Messers Prince and Kim discovered that inactivation could be carried out without this dilution and, thus, the preferred mode of carrying out the invention is to effect the inactivation upon purified and undiluted HBsAg. This preferred mode of proceeding, which also produces the described improved morphological forms of HBsAg, is the subject of a separate patent application to be filed in the names of Messers Prince and Kim.

We contemplate that the principles of this invention, i.e., enhancement of immunogenicity of a lipid membrane immunogen by flash heat inactivation of highly concentrated purified membrane preparations will be readily applicable to the enhancement of the effectiveness, and/or reduction in required dose, of other vaccines such as recombinant DNA derived vaccines produced in eukaryotic cells, e.g., yeast or cell culture derive recombinant DNA based hepatitis B and other vaccines, as well as present killed vaccines such as that for influenza, rabies, rubeola, herpes group viruses, retroviruses such as HTLV I, II and III, parasitic vaccines and others now available or in the process of development.

Figure 1:
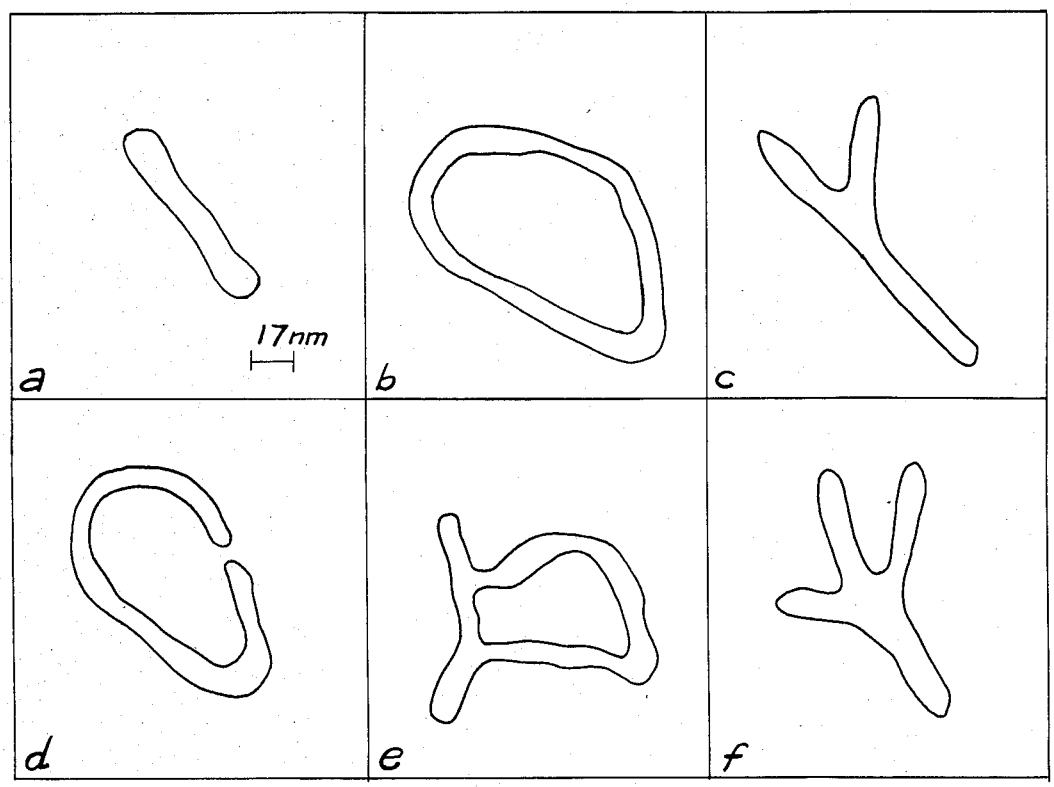
FIG. 1 is a schematic diagram illustrating the filamentous forms produced from small spherical particles by flash heating: a. linear filament; b. closed circular or ring shaped filament; c. branched filament; d. open circular filament; e. branched circular filament; f. multiple branched filament.

What is claimed is:

1. A proteinaceous mass comprising particles of HBsAg, said particles being branched ring-shaped as depicted in FIG. 1b, open ring-shaped as depicted in FIG. 1d, or ring-shaped branched as depicted in FIG. 1e.

2. A proteinaceous mass according to claim 1 wherein said filaments have a diameter of 15 to 20 nm.

3. A proteinaceous mass according to claim 1 containing less than 5% by weight of blood serum proteins, other than sodium caprylate stabilized human serum albumin.

4. A proteinaceous mass according to claim 3 which is substantially free of blood serum proteins.

5. A proteinaceous mass according to claim 1 wherein said proteinaceous mass has ring-shaped filamentous HBsAg containing particles having in addition filaments protruding outwardly from said closed circular filament.

6. A proteinaceous mass according to claim 5 wherein said filamentous particles have a length of at least 50 nm.

7. A proteinaceous mass according to claim 6 wherein said filamentous particles have a length of between 100 and 1000 nm.

8. A proteinaceous mass according to claim 1 having an immunogenicity at least 4 fold greater than a composition consisting essentially of HBsAg in the form of spherical particles of a size of 18 to 24 nm.

9. A proteinaceous mass according to claim 8 wherein said proteinaceous mass has an immunogenicity of between 6 and 30 times that of a proteinaceous mass consisting essentially of spherical HBsAg particles of a size of 18 to 24 nm.

10. A proteinaceous mass according to claim 8 which contains less than 5% by weight of other blood serum proteins, other than sodium caprylate stabilized human serum albumin.

11. A proteinaceous mass according to claim 10 which is substantially free of other blood serum proteins.

12. A Proteinaceous mass, said proteinaceous mass is produced by:
A. precipitating HBsAg from blood plasma by contacting the same with polyethylene glycol to separate HBsAg from other serum proteins contained therein;
B. effecting negative adsorption separated HBsAg on hydroxylapatite;
C. subjecting the so adsorbed HBsAg to isopynic centrifugation; and
D. subjecting the particles so separated by said centrifugation to heat inactivation by heating the same while in a concentration of at least 0.1 mg/ml at a temperature of 101° to 104° C. for 1 to 15 minutes and thereafter cooling the particles, said heating being conducted at elevated pressure when said heating is continuous flow flash heating.

13. A proteinaceous mass according to claim 12 wherein said particles are treated with detergent prior to heating, thus raising their mean aqueous density in sucrose gradients from 1.200 to 1.224 gm/cc.

14. A proteinaceous mass according to claim 12 wherein said particles are heated at 101° to 104° C. while being passed through a tube immersed in a heated medium, said tube having a diameter of 0.1 to 10 mm.

15. A proteinaceous mass according to claim 14 wherein a pressure of 800 to 1000 mm Hg is applied to said particles while being passed through said tube to obtain a residence time of said particles in said tube of between 1 and 15 minutes.

16. A proteinaceous mass according to claim 12 wherein said HBsAg particles are diluted with sodium caprylate stabilized human serum albumin prior to said heat treatment.

17. A proteinaceous mass according to claim 12 wherein the concentration of said HBsAg particles in the solution subjected to heat treatment is at least 0.1 mg/ml.

18. A proteinaceous mass according to claim 17 wherein the concentration of HBsAg particles in the serum subjected to said heat treatment is between 0.1 and 10 mg/ml.

19. A proteinaceous mass according to claim 1 wherein said filamentous structure is a branch structure with at least one of the branches of the structure having a length of at least 50 nm.

20. A proteinaceous mass according to claim 1 wherein there are at least three branches to said filamentous structures.

21. A proteinaceous mass according to claim 1, wherein said filaments are branched and have diameters of 15 to 20 nm and lengths of at least 50 nm.

22. A vaccine comprising the proteinaceous mass of claim 1 and a physiologically acceptable diluent.

23. A vaccine comprising the proteinaceous mass of claim 2 and a physiologically acceptable diluent.

24. A vaccine comprising the proteinaceous mass of claim 3 and a physiologically acceptable diluent.

25. A vaccine comprising the proteinaceous mass of claim 5 and a physiologically acceptable diluent.

26. A vaccine comprising the proteinaceous mass of claim 6 and a physiologically acceptable diluent.

27. A vaccine comprising the proteinaceous mass of claim 13 and a physiologically acceptable diluent.

28. A vaccine comprising the proteinaceous mass of claim 2 and a physiologically acceptable diluent.

29. A vaccine comprising the proteinaceous mass of claim 11 and a physiologically acceptable diluent.

30. A vaccine comprising the proteinaceous mass of claim 19 and a physiologically acceptable diluent.

31. A vaccine comprising the proteinaceous mass of claim 20 and a physiologically acceptable diluent.

32. A process for producing a proteinaceous mass according to claim 1 which comprises the steps of:
  A. precipitating HBsAg from blood plasma by contacting the same with polyethylene glycol to separate HBsAg from other serum proteins contained therein;
  B. effecting negative adsorption of separated HBsAg on hydroxylapatite;
  C. subjecting the so adsorbed HBsAg to isopynic centrifugation; and
  D. subjecting the particles so separated by said centrifugation to heat inactivation by heating the same while in a concentration of at least 1 mg/ml under 800–1000 mm Hg pressure at a temperature of 101° to 105° C. for 1 to 15 minutes and thereafter cooling the so heated particles.

33. A process according to claim 32 wherein the particles are heated in a tube of diameter 0.1 to 10 mm which tube is suspended in a heating medium for between 1 and 15 minutes at 101° to 105° C., at a pressure of 800–1000 mm Hg.

34. A vaccine according to claim 22 which is substantially free of serum proteins, detectable HBV DNA and contains HBsAg, HBeAg and pre-S antigenic determinants.

35. A process for inducing antibodies in an animal which comprises introducing into said animal a proteinaceous mass according to claim 1.

36. A process for inducing antibodies in an animal which comprises introducing into said animal a proteinaceous mass according to claim 2.

37. A process for inducing antibodies in an animal which comprises introducing into said animal a proteinaceous mass according to claim 3.

38. A process for inducing antibodies in an animal which comprises introducing into said animal a proteinaceous mass according to claim 4.

39. A process for inducing antibodies in an animal which comprises introducing into said animal a proteinaceous mass according to claim 13.

40. A process according to claim 35 wherein said animal is a human.

41. A proteinaceous mass according to claim 1, containing one or more branched particles.

42. A proteinaceous mass according to claim 1, comprising ring-shaped particles as depicted in FIG. 1b.

43. A proteinaceous mass according to claim 1, comprising open ring-shaped particles as depicted in FIG. 1d.

44. A proteinaceous mass according to claim 1, comprising ring-shaped branched particles as depicted in FIG. 1e.

* * * * *

UNITED STATES PATENT AND TRADEMARK OFFICE
CERTIFICATE OF CORRECTION

PATENT NO. : 4,639,371

DATED : January 27, 1987

INVENTOR(S) : Alfred M. Prince, et al.

It is certified that error appears in the above-identified patent and that said Letters Patent is hereby corrected as shown below:

| | |
|---|---|
| Col. 11, line 68 | Change "derive" to --derived--ments-- |
| Col. 12, line 23-24 | After "said" delete "closed circular" and substitute --ring-shaped-- |
| Col. 12, line 48 | After "A" delete "Proteinaceous" and substitute --proteinaceous-- |
| Col. 14, line 15 | Before "for" delete "105°" and substitute --104°-- |
| Col. 14, line 20 | After "to" delete "105°" and substitute --104°-- |

Signed and Sealed this

Twenty-sixth Day of January, 1988

Attest:

DONALD J. QUIGG

Attesting Officer     Commissioner of Patents and Trademarks

UNITED STATES PATENT AND TRADEMARK OFFICE
CERTIFICATE OF CORRECTION

PATENT NO. : 4,639,371

DATED : January 27, 1987

INVENTOR(S) : Alfred M. Prince, et al.

It is certified that error appears in the above-identified patent and that said Letters Patent is hereby corrected as shown below:

Col. 12, line 8            After "branched" insert --filaments,--

Col. 12, line 10           After "branched" insert --filaments--

Col. 14, line 44           After "branched" insert --filament--

Signed and Sealed this

Thirty-first Day of May, 1988

Attest:

DONALD J. QUIGG

*Attesting Officer*         *Commissioner of Patents and Trademarks*

UNITED STATES PATENT AND TRADEMARK OFFICE
CERTIFICATE OF CORRECTION

PATENT NO. : 4,639,371

DATED : January 27, 1987

INVENTOR(S) : Alfred M. Prince, et al.

It is certified that error appears in the above-identified patent and that said Letters Patent is hereby corrected as shown below:

Col. 14, line 13          Delete "1" and substitute --.1--

Signed and Sealed this

Twenty-third Day of May, 1989

Attest:

DONALD J. QUIGG

*Attesting Officer*          *Commissioner of Patents and Trademarks*